United States Patent [19]

Wheeler

[11] Patent Number: 4,786,651

[45] Date of Patent: Nov. 22, 1988

[54] TREATMENT OF CUTANEOUS HYPERPROLIFERATIVE DERMATOSES WITH MANOALIDE

[75] Inventor: Larry Wheeler, Irvine, Calif.

[73] Assignee: Allergan, Inc., Irvine, Calif.

[21] Appl. No.: 825,309

[22] Filed: Feb. 3, 1986

[51] Int. Cl.$^4$ .................... A61K 31/35; A61K 31/34
[52] U.S. Cl. .................................... 514/460; 514/473
[58] Field of Search ............................... 514/460, 473

[56] References Cited

U.S. PATENT DOCUMENTS 4,447,445 5/1984 Jacobs et al. .................... 514/460

Primary Examiner—Jerome D. Goldberg
Attorney, Agent, or Firm—James M. Kanagy; Stuart R. Suter

[57] ABSTRACT

Manoalide and its derivatives are useful in the treatment of cutaneous hyperproliferative dermatoses.

2 Claims, 2 Drawing Sheets

TREATMENT OF CUTANEOUS HYPERPROLIFERATIVE DERMATOSES WITH MANOALIDE

BACKGROUND

Manoalide and its derivatives have been found to be useful in the treatments of cutaneous hyperproliferative dermatoses. Manoalide, when applied topically or systemically can inhibit ornithine decarboxylase (ODC), an important rate limiting enzyme in cellular growth. When skin cells, keratinocytes, are incubated with manoalide in vitro, there is a dose dependent inhibition of DNA synthesis. More particularly, application of manoalide is of therapeutic benefit in dermatoses involving benign or malignant hyperplasia such as psoriasis or skin cancers.

Ornithine decarboxylase (ODC) is a key regulatory enzyme in normal and neoplastic growth (D. H. Russell, Drug Metabol. Reviews 16, 1-88, 1985). ODC converts ornithine to putrescine and is the initial and rate limiting enzyme in the polyamine biosynthetic pathway. Polyamines (putrescine, spermidine, spermine) are the organic cations of the cell and accumulate in tissues in response to a growth stimulus (D. H. Russel and P. J. Stanbrook, Proc. Natl. Acad. Sci. USA 72, 1482, 1975; D. H. Russell and C. C. Levey, Cancer Res 31, 248, 1971; D. H. Russell and T. A. McVickers, Biochem Biophys. Acta, 259, 247, 1972). It has been amply demonstrated that ODC activity is elevated in proliferating cells and is induced in the epidermis by trophic hormones, mitogens, carcinogens and tumor promoters such as 12-O-tetra-decanoylphorbol-13-acetate (TPA).

The hallmark of many skin diseases is epidermal hyperproliferation. Psoriasis, for example is a hereditary skin disease. Persons with psoriasis develop skin lesions, either spontaneously or at sites of cutaneous damage, which show seemingly uncontrolled non-malignant growth of the epidermis. It is thought that this increased epidermal cell proliferation is an essential component of the pathophysiology of psoriasis. Russell et al. (J. Invest. Dermatol. 71, 177, 1977) has shown that ODC in psoriatic lesions was approximately six fold higher than in uninvolved skin. Elevations in putrescine, spermidine and spermine were also observed.

It has now been found that manolide and its analogs have the capacity to effectively modify epidermal ODC and thereby affect such diseases as psoriasis and neoplasias affected by modification of ODC activity.

SCOPE OF THE INVENTION

Manoalide has been isolated from the marine sponge *Laffariella variabilis* by E. D. de Silva and P. J. Scheur; Tetrahedron Letters Vol 21, pp 1611-1615 Perganon Press Ltd. 1980. It has the following structure.

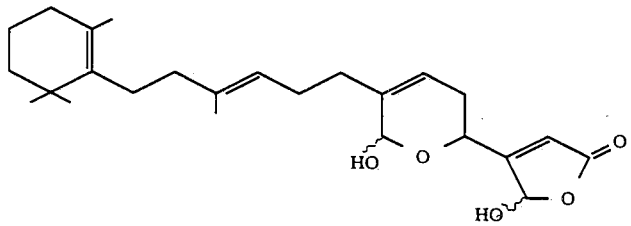

This compound has been disclosed, for example, in U.S. Pat. No. 4,447,445 describing a new medical use as an anti-inflammatory analgesic of marine origin. Synthetic analogs of manoalide have been prepared which are intended to be within the scope of this invention. Manoalide and these synthetic analogs can be generically represented by the formula:

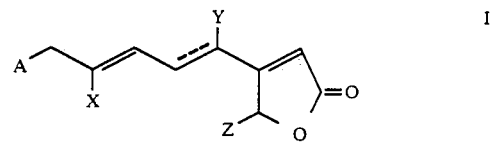

wherein
X is —CH$_3$, —CH$_2$OH, —CHO, OR —COOH;
Y is —H or —OH;
Z is —H or —OH; and
The dotted line represents either a single bond or a double bond which may be in either the E or Z configuration; and
A is R$_m$ or R$_n$

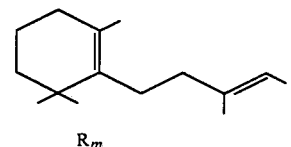

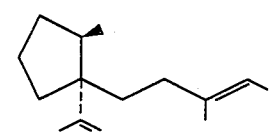

X is CHO or COOH, of formula I includes the hemiacetal or delta-lactone, respectively.

When X is —COOH, the compounds of formula II may be in the form of the corresponding alkyl esters, such esters derived from alcohols of 1 to 10 carbon atoms. When X is —CH$_2$OH and/or Y is —OH and/or Z is —OH, the compounds of formula I may be in the form of the acyl esters of acids from 1 to 10 carbon atoms.

Also included are the pharmaceutically acceptable salts of those compounds where X is —COOH.

SUMMARY OF THE INVENTION

This invention is for a method of treating psoriasis, which method comprises administering to a mammal a therapeuticaly effective amount of a compound of formula I, either alone or in combination with a pharmaceutically acceptable excipient.

DESCRIPTION OF THE PREFERRED EMBODIMENTS

Figure 1:
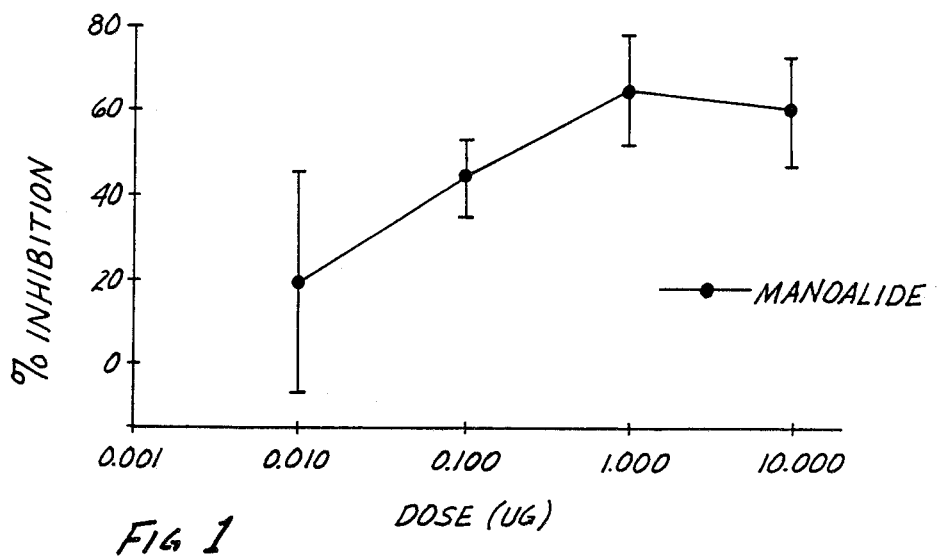

Compounds of the invention which contain alcohols may conveniently be esterified with acyl groups containing 1–6 carbon atoms using methods standard in the art. Suitable acyl groups include acetyl, propanoyl, n-hexanoyl, 4-methylpentanoyl, and the like. The acyl groups may also be unsaturated, and thus also included are acryloyl, methyl acryloyl, 3-methylbuten-2-oyl, and so forth.

In addition, for those embodiments wherein X is carboxyl and are not in a lactone form, the esters of the free carboxyl groups are also included in the invention. These are esters of the saturated or unsaturated alcohols, such as, for example, ethanol, N-butanol, cyclohexanol, cyclopentanol, 3-methylbuten-2-ol, i-propanol, and the like.

The esters of the compounds of formula I containing alcohol constituent may be prepared using standard techniques, such as treating the alcohol-containing compounds of the invention with the free acid forms of the desired acyl substituent in the presence of a strong acid such as boron trifluoride, hydrogen chloride, or sulfuric acid. (They may also be formed from the activated forms of the acyl groups, such as the acyl chlorides.) The reaction can be carried out in an inert organic solvent in which the free acids and the alcohols are soluble, such as a hydrocarbon solvent, for example, cyclooctane, cyclohexane, or benzene or a halogenated hydrocarbon solvent such as chloroform or dichloroethane, or an ether solvent such as diethyl ether or tetrahydrofururan. The reaction is conducted at from about 0° C. to the reflux temperature of the reaction mixture, preferably using hydrogen chloride as a catalyst at a temperature for the reaction mixture of 15° C.–35° C.

The esters of carboxyl groups contained in Formula 1, i.e., when X is COOH, are prepared in a similar manner, except using the appropriate alcohol as reagent.

The product is isolated by conventional means, such as dilution of the reaction mixture with water and extraction at a suitable pH with a water immiscible organic solvent.

Certain of the compounds of the invention contain chiral centers, and accordingly may be prepared as enantiomeric or diastereomeric mixtures or in optically pure form. Unless otherwise specified herein, the preparations are racemates at each chiral center. However, the scope of the invention is not to be considered as limited to these forms, but also to encompass the individual optical isomers of the compounds. When the chiral center corresponds to a chiral center in the natural product analogs, the naturally occurring chirality is preferred.

Similarly, the double bonds may be present in the Z or E forms or mixtures thereof. However, the stereochemistry corresponding to that of the analogous natural product is preferred.

PREFERRED EMBODIMENTS

The following compounds are illustrative of particularly preferred embodiments of the invention. The table below lists the substituents and, where available, the trivial names associated with these substituents. In several cases, both the open chain and cyclic forms (lactones aor hemiacetals) are included. The symbols $R_m$ and $R_n$ refer to the terpenoid substituents set forth above.

| A | X | Y | Z | — | Trivial Name |
|---|---|---|---|---|---|
| $R_m$ | CH$_2$OH | OH | H | single | manoalide diol |
| $R_m$ | COOH (free acid) | OH | OH | single | — |
| $R_m$ | COOH (lactone) | OH | OH | single | manoalide δ-lactone |
| $R_m$ | CHO | H | OH | double(E) | dehydro-seco-manoalide |
| $R_m$ | CHO (hemiacetal) | OH | H | single | — |
| $R_m$ | CH$_3$ | H | OH | double(E) | — |
| $R_m$ | CH$_3$ | H | OH | single | luffariellolide |
| $R_m$ | CH$_3$ | OH | H | single | — |
| $R_m$ | CHO (hemiacetal) | OH | OH | single | manoalide |
| $R_m$ | CHO | OH | OH | single | seco-manoalide |
| $R_n$ | CH$_2$OH | OH | H | single | — |
| $R_n$ | COOH (free acid) | OH | OH | single | — |
| $R_n$ | COOH (lactone) | OH | OH | single | — |
| $R_n$ | CHO | H | OH | double(E) | — |
| $R_n$ | CHO (hemiacetal) | OH | H | single | — |
| $R_n$ | CH$_3$ | H | OH | double(E) | — |
| $R_n$ | CH$_3$ | H | OH | single | — |
| $R_n$ | CH$_3$ | OH | H | single | — |
| $R_n$ | CHO (hemiacetal) | OH | OH | single | luffariellin A |
| $R_n$ | CHO | OH | OH | single | luffariellin B |

UTILITY AND ADMINISTRATION

The compounds of the invention are shown hereinbelow to be active in treating cutaneous hyperproliferative dermatoses. Accordingly, these compounds are useful in the control of psoriasis, acne. For use in this regard, the compounds of the invention are administered to mammals, including humans, in an effective amount of 0.5 to 50 mg per day per kilogram of body weight. The drugs may be administered orally, or topically, or by other standard administration routes. Standard methods for formulating pharmaceuticals of this type may be found in *Remington's Pharmaceutical Sciences*, Mack Publishing Company, Easton, PA (latest edition).

For oral administration, suitable excipients include mannitol, lactose, starch, magnesium stearate, talcum, glucose, magnesium carbonate, and so forth. Oral compositions take the form of solutions, suspensions, tablets, pills, capsules, powders, sustained release formulations, and the like.

Topical administration may be by salve, ointment, spray, powder or the like. Such formulations may be obtained from Remington's Pharmceutical Sciences or numerous other publications on the formulation arts.

The following examples are intended to illustrate the invention and are not limiting. Parts and percentages are given by weight unless otherwise indicated.

EXAMPLE 1

Preparation of 3,7-Bis(hydroxymethyl)-4-hydroxy-11-methyl-13-(2,6,6-trimethylcyclohexenyl)-2,6,10-tridecatrienoic acid γ-lactone (manoalide diol)

A. Excess sodium borohydride (300 mg, 7.0 mM) was added in small portions to a stirred solution of manoalide (136 mg, 0.33 mM) in isopropanol (20 mL) at 0° C. for one hour. Excess reagent were destroyed by dropwise addition of 2% hydrocloric acid until hydrogen evolution ceased. The product was partitioned between water (100 mL) and ether (2×100 mL), the ether extract dried over sodium sulfate and then solvent removed to obtain an oil. The product was purified by HPLC to obtain the diol. Yield 75 mg (55% theoretical); oil*; $^1$H NMR (CDCl$_3$) δ 0.99 (s, 6H), 1.60 (s, 3H), 1.65 (s, 3H), 4.11 (d, 1H, J=14 Hz), 4.17 (d, 1H, J=14 Hz), 5.39 (t, 1H, J=7 Hz), 5.98 (br s, 1H); HRMS. m/z 402.2770, C$_{25}$H$_{38}$O$_4$ requires 402.2770.

*IR(film) 3350, 1775 cm$^{-1}$

B. Manoalide diol, as prepared in paragraph A, is dissolved in acetic anhydride in threefold molar excess in the presence of base, and the mixture stirred at room temperature for several hours. The solvents are then removed and the residue dissolved in ether and filtered to obtain a clear filtrate. Crystals of the diacetate are obtained from the filtrate. In a similar manner, but substituting for acetic anhydride the halides of the appropriate carboxylic acids, the proprionate, dipropionate, hexanoate, and dipentanoate are prepared.

EXAMPLE 2

Preparation of manoalide δ-lactone

A solution of Jones' reagent (prepared from chromium trioxide) [6 mL] was added dropwise to a stirred solution of manoalide (30. mg, 0.07 mM) in distilled acetone (20 mL) at 25° C. until the siolution remained brown. After five minutes, the reaction mixture was filtered through a short column of silica gel and the solvent evaporated to obtain an oil. The product was chromatographed by HPLC to obtain the manoalide δ-lactone as a mixture of two diastereoisomers. Yield 15 mg (50% theoretical); oil*; $^1$H NMR (CDCl$_3$) δ 0.99 (s, 6H), 1.60 (s, 3H), 1.65 (s, 3H), 5.10 (m, 1H), 5.26 (dd, 0.5H, J=12, 5 Hz), 5.37 (dd, 0.5H, J=12, 5 Hz), 6.15 (s, 0.5H), 6.20 (d, 0.5H, J=7 Hz), 6.23 (s, 0.5H); HRMS. m/z 414.2384, C$_{25}$H$_{34}$O$_5$ requires 414.2406.

Manoalide δ-lactone is an inseparable 1:1 mixture of diastereoisomers resulting from epimerization at the hemiacetal carbon atom.

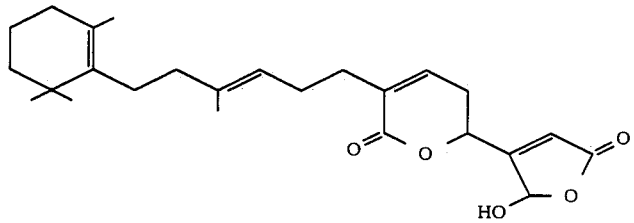

*IR (film) 3300, 1700, 1740 cm$^{-1}$; UV(MeOH) 208.5 nm (ε 10,350)

EXAMPLE 3

Preparation manoalide δ-lacetone acetate

A. Manoalide δ-lactone (15 mg, 0.04 mM) was dissolved in acetic anhydride (0.5 mL) and pyridine (1.0 mL) and the mixture was stirred at 25° C. for four hours. The solvents were removed under high vacuum and the residue dissolved in ether and filtered through a silica gel plug to obtain a clear oil. The oil was chromoatographed by HPLC to obtain a mixture of diastereosisomeric acetates. Yield 16 mg (quantitative); oil;* $^1$H NMR (CDCl$_3$) δ 0.99 (s, 3H), 1.59 (s, 3H), 1.65 (s, 3H), 2.18 (s, 3H), 5.10 (t, 1H, J=7 Hz), 5.21 (m, 1H), 6.26 (s, 0.4H), 6.34 (s, 0.6H), 6.61 (m, 1H), 6.98 (s, 1H), HRMS. m/z 456.2514, C$_{27}$H$_{36}$O$_6$ requires 456.2512.

Manoalide δ-lactone acetate is a 6:4 mixture of two diastereoisomers. The diastereoisomers can be separated, but the material assayed was the mixture of isomers.

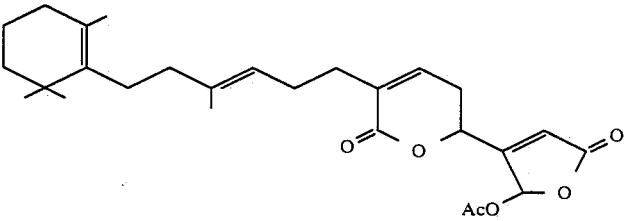

*IR(film) 1880, 1770, 1725 cm$^{-1}$; UV(MeOH) 208 nm (ε 10,600).

B. In a manner similar to that set forth in Paragraph A, but substituting for acetic anhydride, the anyhydrides or halides of proprionic, butanoic, pentanoic, or hexanoic acid, the corresponding manoalide δ-lactone proprionate, butanoate, pentanoate, and hexanoate are prepared.

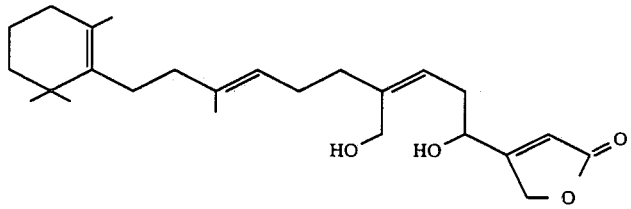

EXAMPLE 4

Isolation and Characterization of Dehydro-seco-manoalide

Examination of UV and $^1$H NMR data of the crude extracts of the sponge *Luffariella variabilis* provide evidence that dehydro-sec-manoalide is present presumably by acid-catalyzed dehydration of manoalide on silica during chromatographic purification of these extracts.

The isolation and purification of manoalide may utilize two or three chromatographic separations on silica gel. Fractions that eluted before manoalide were saved and certain fractions, distinguished by their $^1$H NMR spectra, combined. The combined fractions were chromatographed by LC on μ-Porasil using diethyl ether as eluant to obtain dehydro-manoalide as a viscous yellow oil. The yield is variable.

UV (EtOH) 316 nm (ε 12,000), 205 nm (ε 10,300)
UV (EtOH+NaOH) 461 nm (ε 25,000), 280 nm (ε 1600), 246 (ε 2000)
IR (CHCl$_3$) 1745 cm$^{-1}$, 1670 cm$^{-1}$
$^1$H NMR (CDCl$_3$) δ 0.96 (s, 6H), 1.56 (s, 3H), 1.60 (s, 3H), 5.11 (br t, 1H, J=7 Hz), 6.14 (s, 1H), 6.32 (s, 1H), 6.82 (d, 1H, J=15.5 Hz), 6.91 (d, 1H, J=6 Hz), 7.34 (dd, 1H, J=15.5, 6 Hz), 9.52 (s, 1H).
$^{13}$C NMR (CDCl$_3$) δ 194.3 (d), 171.5 (s), 160.0 (d), 146.3 (s), 145.8 (d), 137.8 (s), 136.8 (s), 133.8 (s), 128.3 (d), 126.9 (s), 121.8 (d), 119.5 (d), 97.8 (d), 40.1 (t), 39.7 (t), 34.8 (s), 32.6 (t), 29.5 (t), 28.5 (q), 28.5 (q), 27.7 (t) 24.6 (t), 19.7 (q), 19.4 (t), 16.0 (q).

Mass spectrum, m/z (%), 398 (3), 380 (3), 251 (6), 137 (100).

Mass measurement, m/z=398.2429, C$_{25}$H$_{34}$O$_4$ requires 398.2457

Using methods analogous to those of Example 3, Paragraph B, and standard in the art, the acetate, formate, hexanoate, and pentanoate esters of dehydro-seco-manoalide are prepared.

EXAMPLE 5

Isolation and Characterization of 3-(4,8-dimethyl-10-(2,6,6-trimethylcyclohexenyl)-deca, 7-dienyl)-4-hydroxybutenolide (Luffariellolide)

A previously unidentified sponge was collected by hand using SCUBA (−15 to −20 m) at Palau, Wester Caroline Islands in January, 1985 and stored frozen. The specimen was defrosted and blended in a high-speed blender with hexane (700 mL) for 2 minutes. the resulting suspension was vigorously stirred for 30 minutes and then filtered. Fresh hexane (700 mL) was added and the mixture was again stirred for 30 minutes and filtered. The combined hexane extracts were evaporated to obtain a brown oil (14.43 q). A portion of the oil was purified by chromatography on silica (MPLC) using hexanes:EtOAc (4:1) to obtain luffariellolide as a colorless oil.

UV: (CH$_3$OH) 214 nm (ε 10,000), (CH$_3$OH/OH$^-$) 253 nm (ε 4400);
$^H$NMR (CDCl$_3$) δ 6.01 (br s, 1H), 5.85 (br s, 1H), 5.14 (br t, 2H, J=7 Hz), 1.64 (br s, 6H), 1.60 (br s, 3H), 0.99 (s, 6H); $^{13}$C NMR (CDCl$_3$) δ 171.9 (s), 169.9 (s), 136.9 (s), 136.8 (s), 136.0 (s), 126.6 (s), 123.1 (d), 121.9 (d), 117.0 (s), 99.5 (d), 40.1 (t), 39.7 (t), 39.5 (t), 34.8 (s), 32.6 (t), 28.5 (q), 27.8 (t), 27.7 (t), 26.4 (t), 24.9 (t), 19.7 (q), 19.4 (t), 16.0 (q), 15.9 (q);

High resolution mass spectrum, obsd. m/z 386.2821, C$_{25}$H$_{38}$O$_3$ requires 386.2821.

EXAMPLE 6

Isolation and Characterization of Luffariellin A and Luffariellin B

About 5% of the specimens of *Laffariella variabilis* collected at Palau during the period 9 Jan. 1985 and 23 Jan. 1985 contained two new compounds, luffariellin A and luffariellin B in place of the normal metabolites manoalide and seco-manoalide. These specimens were identified by extracting a small portion of each specimen and analyzing the $^1$H NMR spectrum of the crude extracts.

The frozen sponge was soaked in methanol overnight, and the methanol was then decanted and filtered. The procedure was repeated 3 times. The combined extracts were evaporated, and the resulting slurry was partitioned between water and dichloromethane (5×250 mL). The combined extracts were dried over anhydrous sodium sulfate and evaporated to obtain a brown oil (670 mg). The oil was filtered through a short column of silica gel in 1:1 hexane/ethyl acetate, then chromatographed on a Lobar B silica column using 25% ethyl acetate in hexane, then 1:1 ethyl acetate/hexane as eluants to obtin luffariellin A (126 mg) and luffariellin B (63 mg).

Luffariellin A: oil;
IR (CHCl$_3$) 3310 (br), 1780, 1762 cm$^{-1}$;
UV (MeOH) 230 nm (4800);
$^1$H NMR (CDCl$_3$) δ 0.7 (d, 3H, J=7 Hz), 1.59 (s, 3H), 1.68 (s, 3H), 4.64 (s, 1H), 4.82 (s, 1H), 4.85 (m, 1H), 5.09 (br t, 1H, J=7 Hz), 5.34 (s, 1H), 5.70 (s, 1H), 6.08 (s, 1H); $^{13}$C NMR (CDCl$_3$) δ 172.0/171.8 (s), 169.0/168.3 (s), 148.0 (s), 137.2/137.0 (s), 136.7 (s), 122.6 (d), 120.9/120.6 (d), 117.8/116.7 (d), 111.6 (t), 98.3/97.8 (d), 91.3/91.1 (d), 63.1/62.3 (d), 55.1 (s), 41.8 (d), 39.6/39.4 (t), 34.8 (t), 34.3 (t), 32.4 (t), 31.0 (t) 29.4 (t), 25.9 (t), 20.7 (t), 20.7 (q), 18.1 (q), 16.2 (q);

Mass spectrum, m/z 398 (M—H$_2$O).

Luffariellin B: oil;

IR (CHCl$_3$) 3350 (br), 1762, 1686 cm$^{-1}$;

UV (MeOH) 226 nm (10,000);

$^1$H NMR (CDCl$_3$) δ 0.70 (d, 3H, J=7 Hz), 1.55 (s, 3H), 1.67 (s, 3H), 4.63 (s, 1H), 4.82 (s, 1H), 5.07 (br t, 1H, J=7 Hz), 5.40 (m, 1H), 6.111 (br s, 2H), 6.56 (t, 1H, J=7 Hz), 9.40 (s, 1H); $^{13}$C NMR (CDCl$_3$) δ 195.2 (d), 171.2 (s), 170.4/169.3 (s), 148.3/148.2 (s), 145.7/145.6 (d), 137.4 (s), 122.2 (d), 118.3 (d), 117.7 (t), 98.3/97.9 (d), 66.8/66.3 (d), 55.1 (s), 41.9 (d), 34.8 (2C, t), 31.0 (t), 29.1 (t), 26.8 (t), 24.5 (t), 20.7 (t), 20.7 (q), 18.1 (a), 16.3 (q);

MS m/z 398 (M—G$_2$O)

Manoalide can also inhibit tape-stripped ODC after systemic administration.

Results from this study gave the following data:

| Treatment | ODC* | % Inhibition |
|---|---|---|
| Vehicle (soybean oil) | 6.1 ± 1.2 | |
| Manoalide** | 2.8 ± 0.6 | 54% (p < .05) |

*nmoles $^{14}$CO$_2$ (mg protein/mg protein/hr)
**50 mg/kg; IP, 30 min before tape-stripping In Vitro Assay Keratinocytes from 1-2 day old neonatal balb/c mice were used. Cells were plated in 35 mm culture dishes in M199 medium containing 10% FCS and incubated at 37° C. in 5% CO$_2$. Cells were allowed to reach confluency at which time 0.01, 0.1, 1.0, 10 and 20 μM manoalide was added in DMSO. Fresh media and drug were added each day to culture for three days. On the fourth day cells were pulsed with $^3$H-thymidine (1 82 Ci/ml)

Luffariellin A

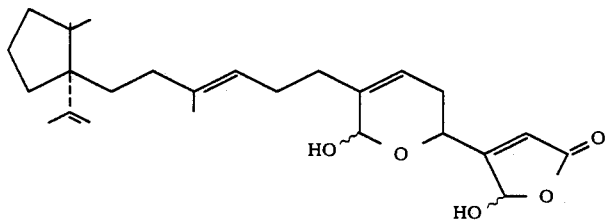

Luffariellin B

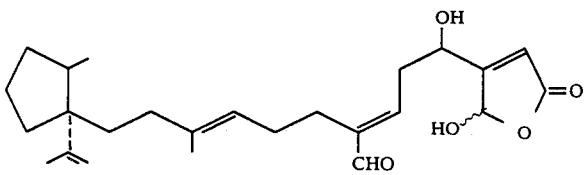

Psoriasis Bioassays

Tape-stripping mouse epidermis is quick and convenient method of inducing ODC activity that avoids the necessity of handling carcinogens. M. Connor and N. Lowe (J. Invest. Dermatol 43, 5174, 1983) have studied the ability of retinoids to inhibit ODC. Trans-retinoic acid, 13-cis retinoic acid, and etretinate were all active at inhibiting ODC and therapeutically active in humans. Therefore, inhibition of tape-stripped ODC is an in vitro method to demonstrate the potential efficacy of drugs for epidermal hyperproliferation such as psoriasis. In vitro methods have also been useful in determining the anti-hyperproliferative activity of drugs. C. Marcelo and J. Tomich (J. Invest. Dermatol. 81, 64s, 1983) have shown that neonatal mouse keratinocyte cultures can be used to identify drugs that inhibit DNA synthesis. More recently, R. Weiss, Eichner, R. and Sunn, T. T, J. Cell Biol., 98: 1397-1406, (1984) have shown that epidermal cultures are in fact, a model of epidermal hyperproliferation and therefore a good model for testing drugs that inhibit hyperporliferation.

In Vivo Assay

Female hairless mice were tape-stripped and ODC activity determined according to the method of M. Connor and N. Lowe (J. Invest. Dermatol. 43, 5174, 1983).

Manoalide applied at the time of or just after tape-stripping inhibits ODC in a dose related fashion with an IC$_{50}$ of 0.25 nmoles (FIG. 1).

to determine how much manoalide inhibited DNA syntheses (CPM/μg DNA).

Figure 2:
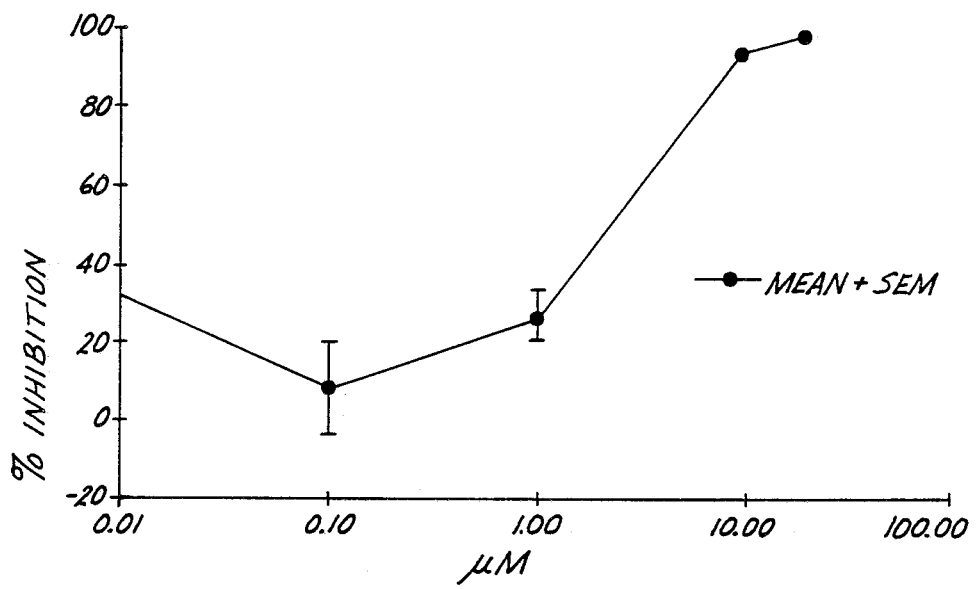

Manoalide was found to inhibit keratinocyte DNA synthesis in a dose related fashion (FIG. 2). Doses from 1-30 μM result in statistically significant inhibition of DNA synthesis compared to vehicle controls.

Figure 3:
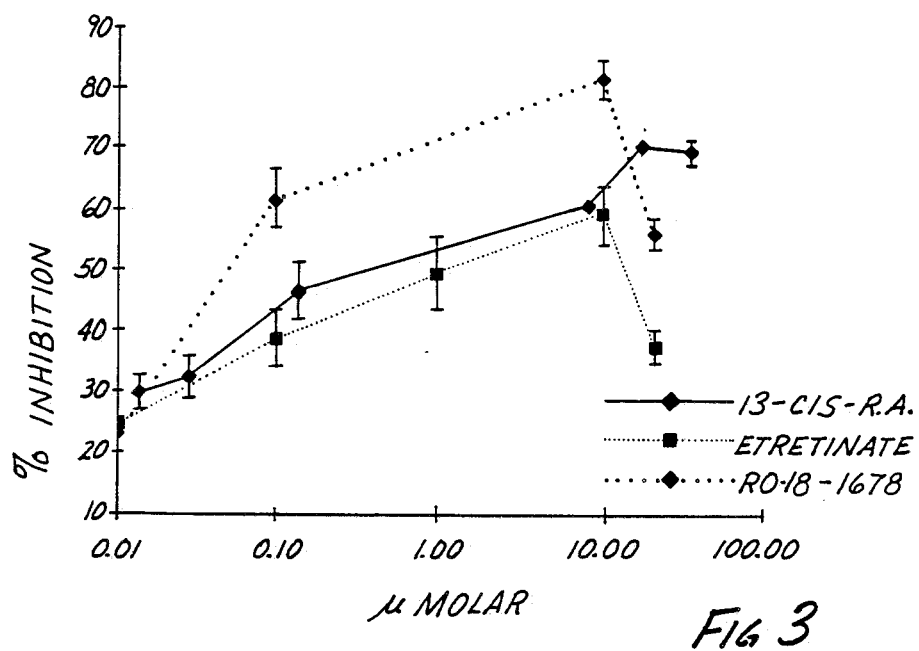
Figure 4:
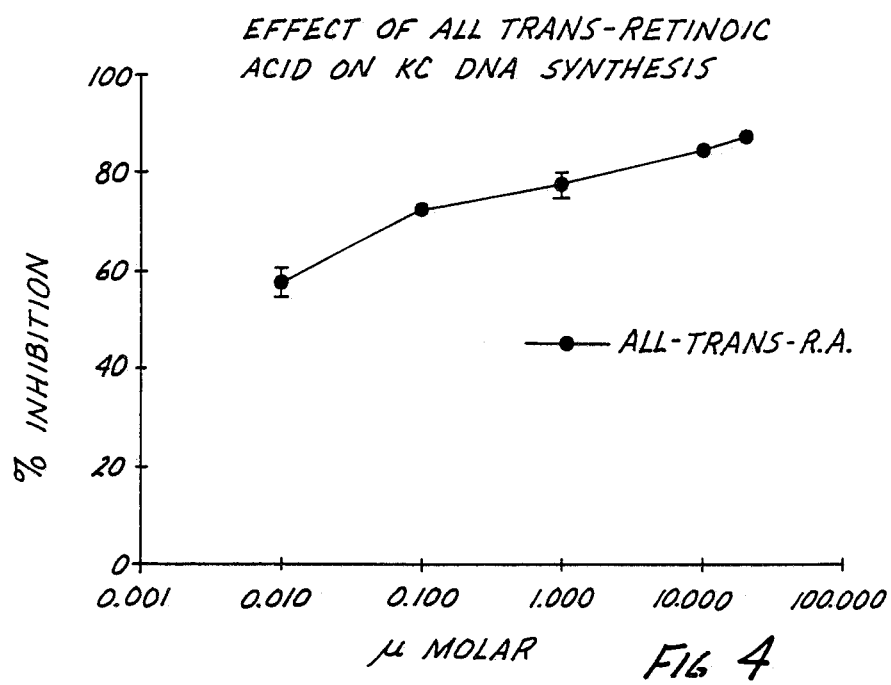

Also shown for comparison on other anti-psoriatic treatment modalities: etretinate, 13-cis retinoic acid, all-trans retinoic acid. (FIGS. 3 and 4)

What is claimed is:

1. A method of treating psoriasis or acne which method comprises administering to a mammal in need of said treatment an amount therapeutically effective for treating psoriasis and acne of a compound of formula I, either alone or in combination with a pharmaceutically acceptable excipient where formula I is

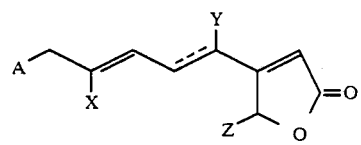

wherein
X is —CH$_3$, —CH$_2$OH, —CHO, OR —COOH;
Y is —H or —OH;
Z is —H or —OH; and the dotted line represents either a single bond or a double bond which may be in either the E or Z configuration; and A is $R_m$ or $R_n$

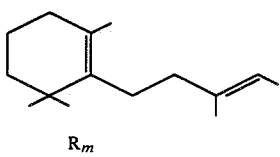

$R_m$

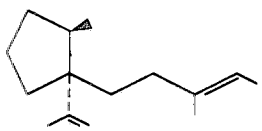

$R_n$ and when Y is —OH and X is —CHO or —COOH, the compound of formula II includes the hemiacetal or delta-lactose, respectively; and when X is —COOH, the corresponding alkyl esters, esters derived from alcohols of 1 to 10 carbon atoms; and when X is —CH$_2$OH and/or Y is —OH and/or Z is —OH, the corresponding acyl esters of acids from 1 to 10 carbon atoms; and the pharmaceutically acceptable salts of those compounds where X or X is —COOH.

2. The method of claim 1 wherein the compound is manoalide.

* * * * *